United States Patent
Garde et al.

(10) Patent No.: US 9,937,308 B2
(45) Date of Patent: Apr. 10, 2018

(54) SYSTEM AND METHOD FOR CUSTOMIZABLE AUTOMATED CONTROL OF FRACTION OF INSPIRED OXYGEN AND/OR POSITIVE END EXPIRATORY PRESSURE TO MAINTAIN OXYGENATION

(75) Inventors: Smita Garde, Irvine, CA (US); Samir Ahmad, San Diego, CA (US); Michael Edward Madison, Carlsbad, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 553 days.

(21) Appl. No.: 13/993,222

(22) PCT Filed: Dec. 6, 2011

(86) PCT No.: PCT/IB2011/055477
§ 371 (c)(1),
(2), (4) Date: Aug. 14, 2013

(87) PCT Pub. No.: WO2012/080903
PCT Pub. Date: Jun. 21, 2012

(65) Prior Publication Data
US 2013/0312754 A1    Nov. 28, 2013

Related U.S. Application Data

(60) Provisional application No. 61/424,382, filed on Dec. 17, 2010.

(51) Int. Cl.
A61M 16/00    (2006.01)
A61M 16/10    (2006.01)

(52) U.S. Cl.
CPC .... *A61M 16/0057* (2013.01); *A61M 16/0069* (2014.02); *A61M 16/024* (2017.08);
(Continued)

(58) Field of Classification Search
CPC .......... A61M 16/0057; A61M 16/0069; A61M 16/0051; A61M 2016/1025;
(Continued)

(56) References Cited

U.S. PATENT DOCUMENTS 5,331,995 A *  7/1994  Westfall ................ A61M 16/00
                                               128/204.21
5,365,922 A * 11/1994  Raemer ................ A61B 5/0833
                                               128/202.22
(Continued)

FOREIGN PATENT DOCUMENTS

| JP | 2004298554 A | 10/2004 |
| WO | 2005051280 A2 | 6/2005 |
| WO | 2006127356 A2 | 11/2006 |

*Primary Examiner* — Annette Dixon (57) ABSTRACT

A pressurized flow of breathable gas is delivered to the airway of a subject in accordance with a therapy regimen. The therapy regimen may be designed to maintain oxygenation of the subject. The therapy regimen dictates levels of fraction of inspired oxygen and/or positive end expiratory pressure to maintain a therapeutically beneficial level of oxygenation in a feedback manner. Within the therapy regimen, changes made to fraction of inspired oxygen and/or positive end expiratory pressure automatically and dynamically are constrained by user configured constraints such as the maximum incremental change, amount of time between adjustments, or the maximum rate of change This may provide a level of customization of the automated control of the therapy regime for individual subjects.

12 Claims, 4 Drawing Sheets

(52) U.S. Cl.
CPC . *A61M 16/1065* (2014.02); *A61M 2016/1025* (2013.01); *A61M 2202/0208* (2013.01); *A61M 2205/505* (2013.01); *A61M 2230/205* (2013.01)

(58) Field of Classification Search
CPC .... A61M 2230/205; A61M 2202/0208; A61M 2205/505; A61M 16/00; A61M 16/0003; A61M 16/0063; A61M 16/0627; A61M 16/0666; A61M 16/0672; A61M 16/08; A61M 16/10; A61M 16/1015; A61M 16/1065; A61M 16/107; A61M 16/12; A61M 16/20; A61M 2016/0027; A61M 2016/0039; A61M 2205/3368; A61M 2205/3561; A61M 2205/3569; A61M 2205/581; A61M 2205/583; A61M 2210/0618; A61M 2210/0625; A61M 2210/0662; A61M 2230/005; A61M 2230/06; A61M 2230/202; A61M 2230/208; A61M 2230/30; A61M 2230/42; A61M 2230/432; A61M 2230/435; A61B 2560/0276; A61B 2562/247; A61B 5/0205; A61B 5/02416; A61B 5/02427; A61B 5/0261; A61B 5/0295; A61B 5/036; A61B 5/08; A61B 5/082; A61B 5/0833; A61B 5/087; A61B 5/0873; A61B 5/097; A61B 5/145; A61B 5/14539; A61B 5/1455; A61B 5/14551; A61B 5/14552; A61B 5/1459; A61B 5/4818; A61B 5/4836; A61B 5/6819; A61B 5/682; A61B 5/6826; A61B 5/6829; A61B 5/7278; A61B 5/7282
USPC ............ 128/204.23, 203.14, 204.18, 204.21, 128/205.11
See application file for complete search history.

(56) References Cited

U.S. PATENT DOCUMENTS

| | | | |
|---|---|---|---|
| 5,388,575 A * | 2/1995 | Taube | ...................... 128/204.23 |
| 5,682,877 A | 11/1997 | Mondry | |
| 6,671,529 B2 | 12/2003 | Claure | |
| 7,008,380 B1 * | 3/2006 | Rees et al. | ..................... 600/532 |
| 7,527,054 B2 | 5/2009 | Misholi | |
| 8,695,593 B2 * | 4/2014 | Tehrani | .................. A61H 31/02 128/204.18 |
| 8,783,248 B2 * | 7/2014 | Heinonen | ............. A61M 16/01 128/203.14 |
| 2005/0109340 A1 | 5/2005 | Tehrani | |
| 2007/0027375 A1 | 2/2007 | Melker | |
| 2008/0314385 A1 | 12/2008 | Brunner | |
| 2010/0224191 A1 | 9/2010 | Dixon et al. | |

* cited by examiner

SYSTEM AND METHOD FOR CUSTOMIZABLE AUTOMATED CONTROL OF FRACTION OF INSPIRED OXYGEN AND/OR POSITIVE END EXPIRATORY PRESSURE TO MAINTAIN OXYGENATION

BACKGROUND

1. Field of the Disclosure

The invention relates to automated control of fraction of inspired oxygen and/or positive end expiratory pressure to maintain oxygenation of a subject.

2. Description of the Related Art

The fraction of inspired oxygen delivered to a subject receiving ventilation therapy is usually adjusted by the clinician (e.g., intensive care physician, therapist, nurse, etc.) to respond to the changes in the subject's oxygenation levels. The need for adjustments and frequency of adjustments of fraction of inspired oxygen depends on the subject's conditions and the availability of the clinician. In NICU, for a premature baby, the adjustments for fraction of inspired oxygen may be more often due to the frequent spontaneous desaturations. For other subjects in ICU the adjustments may be done to respond to the gradual changes (improvement or deterioration) in a subject's condition. This need for the adjustments in fraction of inspired oxygen levels often contributes to substantial workload for the clinicians.

SUMMARY

One aspect of the disclosure relates to a system configured to control the fraction of inspired oxygen in a pressurized flow of breathable gas delivered to the lungs of a subject. In one embodiment, the system comprises a pressure generator, a user interface, and one or more processors. The pressure generator is configured to generate a pressurized flow of breathable gas for delivery to the lungs of a subject, the pressure generator being configured to selectively control the fraction of inspired oxygen of the subject by adjusting the concentration of oxygen in the pressurized flow of breathable gas. The one or more processors are configured to execute computer program modules including a blood oxygen module, an oxygen fraction module, an interface module, and a control module. The blood oxygen module is configured to determine a level of an oxygenation metric representing an amount of oxygen present in the blood of the subject. The oxygen fraction module is configured to determine a therapeutic fraction of inspired oxygen for the subject in accordance with a therapy regimen, wherein the oxygen fraction module is configured to dynamically determine the therapeutic fraction of inspired oxygen based on the oxygenation metric in a feedback manner. The interface module is configured to receive oxygen fraction constraints from a user via the user interface. The oxygen fraction module is further configured such that the oxygen fraction constraints received from the user via the user interface constrain the dynamic determination of the therapeutic fraction of inspired oxygen. The control module is configured to control the pressure generator to adjust the concentration of oxygen in the pressurized flow of breathable gas to control the fraction of inspired oxygen of the subject in accordance with therapeutic fraction of inspired oxygen determined by the oxygen fraction module. The modules may be configured such that the therapy regimen reduces the therapeutic fraction of inspired oxygen and/or a therapeutic positive end expiratory pressure over time to wean the subject.

Another aspect of the invention relates to a method of controlling the fraction of inspired oxygen in a pressurized flow of breathable gas delivered to the lungs of a subject. In one embodiment, the method comprises generating a pressurized flow of breathable gas for delivery to the lungs of a subject; obtaining a level of an oxygenation metric indicating an amount of oxygen present in the blood of the subject; receiving one or more oxygen fraction constraints from a user via a user interface; dynamically determining a therapeutic fraction of inspired oxygen for the subject in accordance with a therapy regimen based on the oxygenation metric in a feedback manner, wherein the oxygen fraction constraints received from the user constrain the dynamic determination of the therapeutic fraction of inspired oxygen; and adjusting the concentration of oxygen in the pressurized flow of breathable gas to control the fraction of inspired oxygen of the subject in accordance with dynamically determined therapeutic fraction of inspired oxygen. The method may include reducing the therapeutic fraction of inspired oxygen and/or a therapeutic positive end expiratory pressure over time in order to wean the subject.

Yet another aspect of the invention relates to a system for controlling the fraction of inspired oxygen in a pressurized flow of breathable gas delivered to the lungs of a subject. In one embodiment, the system comprises means for generating a pressurized flow of breathable gas for delivery to the lungs of a subject; means for obtaining a level of an oxygenation metric indicating an amount of oxygen present in the blood of the subject; means for receiving one or more oxygen fraction constraints from a user via a user interface; means for dynamically determining a therapeutic fraction of inspired oxygen for the subject in accordance with a therapy regimen based on the amount of oxygen present in the blood of the subject in a feedback manner, wherein the oxygen fraction constraints received from the user constrain the dynamic determination of the therapeutic fraction of inspired oxygen; and means for adjusting the concentration of oxygen in the pressurized flow of breathable gas to control the fraction of inspired oxygen of the subject in accordance with dynamically determined therapeutic fraction of inspired oxygen. The system may be configured to reduce the therapeutic fraction of inspired oxygen and/or a therapeutic positive end expiratory pressure over time in order to wean the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not a limitation. In addition, it should be appreciated that structural features shown or described in any one embodiment herein can be used in other embodiments as well. It is to be expressly understood, however, that the drawings are for the purpose of illustration and description only and are not intended as a definition of limits. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
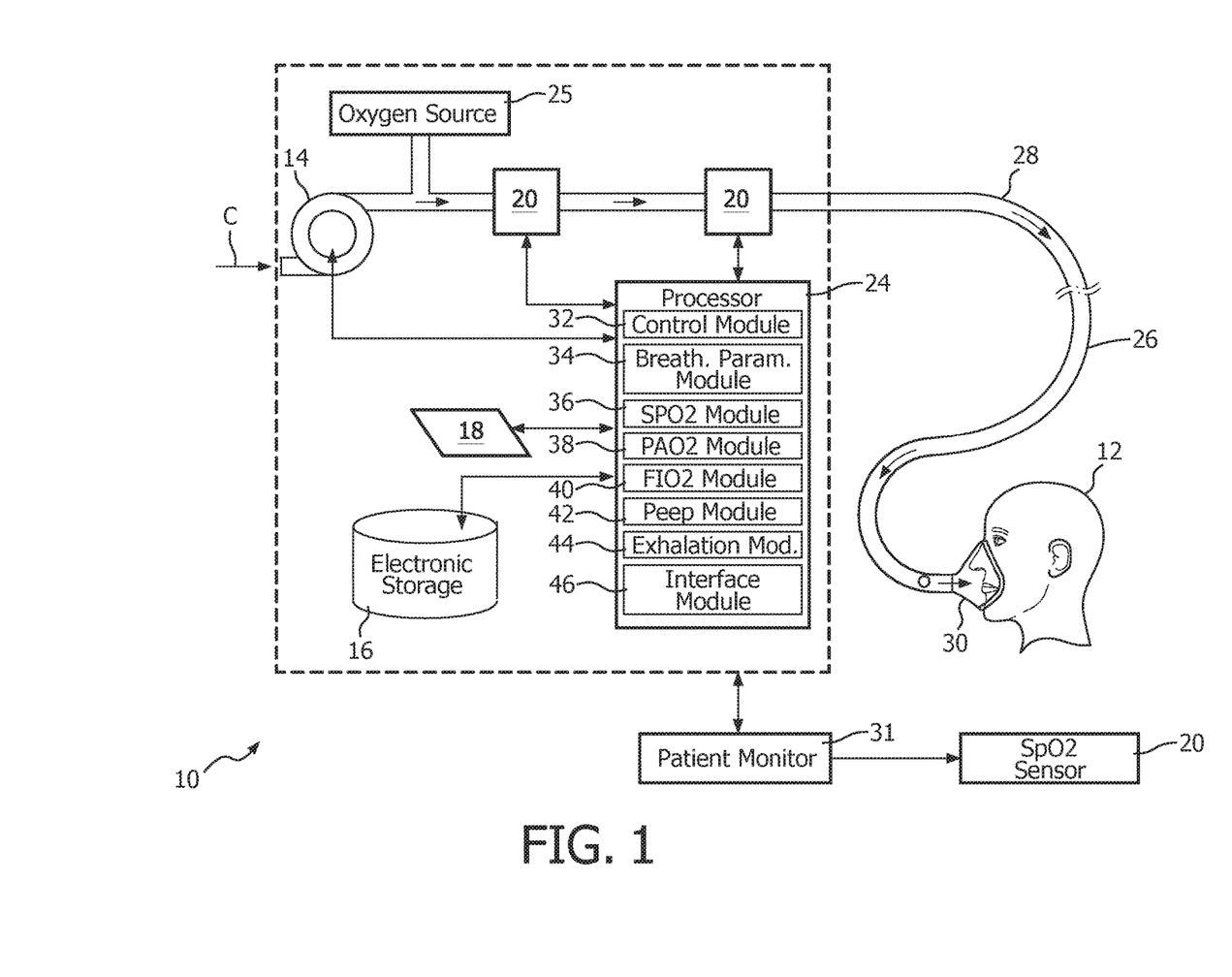
FIG. 1 illustrates a system configured to deliver a pressurized flow of breathable gas to the lungs of the subject in accordance with a therapy regimen.

FIG. 1 illustrates a system 10 configured to deliver a pressurized flow of breathable gas to the lungs of a subject 12 in accordance with a therapy regimen. The therapy regimen may be designed to maintain oxygenation of subject 12. The therapy regimen dictates levels of fraction of inspired oxygen and/or positive end expiratory pressure to maintain a therapeutically beneficial level of oxygenation in a feedback manner. The system 10 is configured such that automatic and dynamic changes made to fraction of inspired oxygen and/or positive end expiratory pressure are constrained by user configured constraints. This may provide a level of customization of the therapy regime for individual subjects. The measurement of oxygenation utilized by system 10 in a feedback manner to control fraction of inspired oxygen may be user selectable. Similarly, the implementation of positive end expiratory pressure control in maintaining oxygenation may be selected and/or deselected by a user. The therapy regimen can be configured by a user to simply maintain oxygenation, or may be configured by the user to wean subject 12 from the therapy provided by system 10. In one embodiment, system 10 includes one or more of a pressure generator 14, electronic storage 16, a user interface 18, sensors 20, a processor 24, and/or other components.

In one embodiment, pressure generator 14 is configured to generate a pressurized flow of breathable gas for delivery to the lungs of subject 12. The pressure generator 14 may control one or more parameters of the pressurized flow of breathable gas (e.g., flow, pressure, volume, humidity, temperature, gas composition, etc.) for therapeutic purposes, or for other purposes. The one or more parameters may be controlled in accordance with a therapy regimen (e.g., as discussed further below). The therapy regimen may be configured to oxygenation in subject 12. By way of non-limiting example, pressure generator 14 may be configured to control the pressure of the pressurized flow of breathable gas in order to maintain a therapeutic inspiratory pressure and/or positive end expiratory pressure. To manage the pressure of the pressurized flow of breathable gas pressure generator 14 may include one or more components that are controllable to manipulate the pressure of the pressurized flow of breathable gas. Such components may include, for instance, a valve, a blower, a bellows, a pressurized gas source, and/or other components for manipulating pressure. The pressure generator 14 is configured to control the concentration of oxygen in the pressurized flow of breathable gas to maintain a therapeutic fraction of inspired oxygen. As such, pressure generator 14 is configured to mix oxygen from oxygen source 25 with another source of breathable gas (e.g., ambient air, wall gas, a canister, and/or other sources) to adjust the concentration of oxygen in the pressurized flow of breathable gas.

The pressurized flow of breathable gas is delivered to the lungs of subject 12 via a subject interface 26. Subject interface 26 is configured to communicate the pressurized flow of breathable gas generated by pressure generator 14 to the lungs of subject 12. As such, subject interface 26 includes a conduit 28 and an interface appliance 30. Conduit conveys the pressurized flow of breathable gas to interface appliance 30, and interface appliance 30 delivers the pressurized flow of breathable gas to the lungs of subject 12. Some examples of interface appliance 30 may include, for example, an endotracheal tube, a tracheal tube, a nasal cannula, a nasal mask, a nasal/oral mask, a full face mask, a total face mask, or other interface appliances that communication a flow of gas with an airway and/or the lungs of a subject. The present invention is not limited to these examples, and contemplates delivery of the pressurized flow of breathable gas to subject 12 using any subject interface.

Although FIG. 1 illustrates the configuration of system 10 with subject interface 26 as being a single-limb, passive exhalation system, this is not intended to be limiting. It will be appreciated that the scope of this disclosure includes embodiments in which the subject interface 26 is formed as a two-limbed system including a second conduit configured to receive exhalation from interface appliance 30. The second conduit connected to an actively controlled exhalation system may exhaust such fluid to atmosphere, may convey such fluid to a filter, and/or convey such fluid to other components including a component within system 10.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 24, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., pressure generator 14, user interface 18, processor 24, etc.).

User interface 18 is configured to provide an interface between system 10 and one or more users (e.g., subject 12, a caregiver, a researcher, a therapy decision-maker, etc.) through which the users may provide information to and receive information from system 10. This enables data, cues, results, and/or instructions and any other communicable items, collectively referred to as "information," to be communicated between the users and one or more of pressure generator 14, electronic storage 16, and/or processor 24. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with pressure generator 14. User interface 18 may be configured to receive input from subject 12 to modify user selectable settings of system 10. For example, the user interface 18 may be configured to change the modes and settings for the ventilation therapy delivered to the subject 12. In another example, the user interface 18 may be configured to set the maximum fraction of inspired oxygen for the system 10, and/or other parameters.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

The sensors 20 include sensors configured to generate output signals conveying information related to gas parameters of the pressurized flow of breathable gas, sensors configured to generate output signals conveying information related to oxygenation of subject 12, and/or other sensors. The gas parameters may include, for example, one or more of a flow, a volume, a pressure, a composition (e.g., concentration(s) of one or more constituents, such as oxygen), humidity, temperature, acceleration, velocity, acoustics, changes in a parameter indicative of respiration, and/or other gas parameters. In one embodiment, sensors 20 include a flow sensor and a pressure sensor. The sensors 20 may include one or more sensors that measure such parameters directly (e.g., through fluid communication with the pressurized flow of breathable gas at pressure generator 14 or in subject interface 26). The sensors 20 may include one or more sensors that generate output signals related to one or more fluid parameters of the pressurized flow of breathable gas indirectly. For example, one or more of sensors 20 may generate an output based on an operating parameter of pressure generator 14 (e.g., a valve driver or motor current, voltage, rotational velocity, and/or other operating parameters), and/or other sensors.

As was mentioned above, sensors 20 may include one or more sensors configured to generate output signals conveying information related to oxygenation of subject 12. The information related to oxygenation may indicate oxygen saturation, partial pressure of oxygen in arterial blood, partial pressure of carbon dioxide in arterial blood, and/or other information related to oxygenation. Such sensors may include sensors that generate output signals conveying information related to oxygenation in an ongoing manner. For example, a sensor generating output signals conveying information related to oxygen saturation may generate output signals in an ongoing manner. Some sensors may require more invasive measurements (e.g., the extraction of blood from subject 12). Such sensors may include sensors measuring partial pressure of oxygen in arterial blood, partial pressure of carbon dioxide in arterial blood, and/or other arterial blood measurements. Measurements that are more invasive to subject 12 (e.g., arterial blood measurements) may be updated at periodic (or substantially periodic) intervals. For example, such measurements may be taken and updated to system 10 at intervals of about 30 minutes, and/or at other intervals.

The sensors 20 may include sensors configured to transmit output signals to one or more of electronic storage 16, user interface 18, and/or processor 24. For example, sensors generating output signals conveying information related to gas parameters of the pressurized flow of breathable gas may transmit output signals to one of more of electronic storage 16, user interface 18, and/or processor 24. The sensors 20 may include sensors configured to transmit output signals to a device or apparatus that is separate from and/or in communication with system 10. For example, sensors generating output signals conveying information related to oxygen saturation and/or partial pressure of oxygen in arterial blood may be coupled with a patient monitor 31 such that output signals from the sensors are transmitted to patient monitor 31. Patient monitor 31 may be configured to process the output signals (e.g., to determine oxygen saturation and/or partial pressure of oxygen in arterial blood). Patient monitor 31 may be communicatively coupled with system 10 to transmit information derived from the output signals, the output signals, and/or other information to system 10. In another example, system 10 may be configured such that sensors generating output signals related to oxygen saturation are coupled to system 10 and may transmit output signals to one or more of electronic storage 16, user interface 18, and/or processor 24. Such transmission may be accomplished via wired and/or wireless transmission. The sensors 20 may include sensors that require measurements to be input manually to system 10 via user interface 18. For example, a sensor measuring partial pressure of oxygen in arterial blood, partial pressure of carbon dioxide in arterial blood, and/or other arterial blood measurements may require the measurements taken to be manually input to system 10.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 14), or processor 24 may represent processing functionality of a plurality of devices operating in coordination. For example, at least some of the functionality attributed herein to processor 24 may be provided by one or more processors associated with patient monitor 31.

As is shown in FIG. 1, processor 24 may be configured to execute one or more computer program modules. The one or more computer program modules may include one or more of a control module 32, a breathing parameter module 34, an oxygen saturation module 36, an arterial oxygen module 38, a oxygen fraction module 40, a PEEP module 42, an exhalation module 44, an interface module 46, and/or other modules. Processor 24 may be configured to execute modules 32, 34, 36, 38, 40, 42, 44, and/or 46 by software; hardware; firmware; some combination of software, hardware, and/or firmware; and/or other mechanisms for configuring processing capabilities on processor 24.

It should be appreciated that although modules 32, 34, 36, 38, 40, 42, 44, and 46 are illustrated in FIG. 1 as being co-located within a single processing unit, in implementations in which processor 24 includes multiple processing units, one or more of modules 32, 34, 36, 38, 40, 42, 44, and/or 46 may be located remotely from the other modules. The description of the functionality provided by the different modules 32, 34, 36, 38, 40, 42, 44, and/or 46 described below is for illustrative purposes, and is not intended to be limiting, as any of modules 32, 34, 36, 38, 40, 42, 44, and/or 46 may provide more or less functionality than is described. For example, one or more of modules 32, 34, 36, 38, 40, 42, 44, and/or 46 may be eliminated, and some or all of its functionality may be provided by other ones of modules 32, 34, 36, 38, 40, 42, 44, and/or 46. As another example, processor 24 may be configured to execute one or more additional modules that may perform some or all of the functionality attributed below to one of modules 32, 34, 36, 38, 40, 42, 44, and/or 46.

The control module 32 is configured to control pressure generator 14 to adjust the parameters of the pressurized flow of breathable gas in accordance with a therapy regimen. The therapy regimen dictates the pressurized flow of breathable gas be provided to the lungs of subject 12 such that the fraction of inspired oxygen be maintained at a therapeutic fraction of inspired oxygen, and/or the positive end expiratory pressure of subject 12 be maintained at a positive end expiratory pressure.

For example, the therapy regimen may be noninvasive ventilation including a bi-level therapy. In such a therapy regimen, the level of pressure of the pressurized flow of breathable gas during exhalation is maintained at an expiratory level (known as Expiratory Positive Airway Pressure or EPAP). During inspirations, the pressure level of the pressurized flow of breathable gas is increased to push gas into the lungs of subject 12. Changes between Inspiration Positive Airway Pressure ("IPAP") and EPAP are triggered in accordance with a respiratory rate, and/or based on spontaneous respiratory effort by subject 12.

The breathing parameter module 34 is configured to determine breathing parameters of subject 12. The breathing parameters are determined by breathing parameter module 34 based on the output signals generated by sensors 20. The breathing parameters determined by breathing parameter module 34 may include one or more of tidal volume, breath rate, minute ventilation, inspiration-to-expiration ratio, resistance and compliance of the lung, respiratory muscle pressure, and/or other breathing parameters and/or other breathing parameters.

The oxygen saturation module 36 is configured to obtain the oxygen saturation of subject 12. Obtaining the oxygen saturation of subject 12 may include determining the oxygen saturation, and/or receiving determinations of oxygen saturation (e.g., from patient monitor 31). The oxygen saturation is determined based on output signals generated by sensors 20. The oxygen saturation sensor is attached to the patients body at a preferred site. The oxygen saturation may be determined, received, and/or otherwise obtained in a substantially ongoing manner (e.g., a sampling rate of less than about 100 miliseconds).

The arterial oxygen module 38 is configured to determine partial pressure of oxygen in arterial blood of subject 12. The determination of partial pressure of oxygen in arterial blood by arterial oxygen module 38 may be an estimation of partial pressure of oxygen in arterial blood that is made in a substantially ongoing manner. This is because partial pressure of oxygen in arterial blood is typically measured directly through the extraction of blood from subject 12. In one embodiment, partial pressure of oxygen in arterial blood is estimated by arterial oxygen module 38 as a function oxygen saturation. Generally, the behavior of oxygen saturation and partial pressure of oxygen in arterial blood are linked such that partial pressure of oxygen in arterial blood at a given moment in time can be estimated based on a measured oxygen saturation.

As has been mentioned above, at various times (e.g., at periodic intervals) arterial blood measurements may be obtained and entered to system 10. Such measurements may include of partial pressure of oxygen in arterial blood, partial pressure of carbon dioxide in arterial blood, blood pH, and/or other measurements. In one embodiment, arterial oxygen module 38 is configured to calibrate or otherwise adjust the determination of partial pressure of oxygen in arterial blood as a function of oxygen saturation when these measurements are obtained by system 10.

Figure 2:
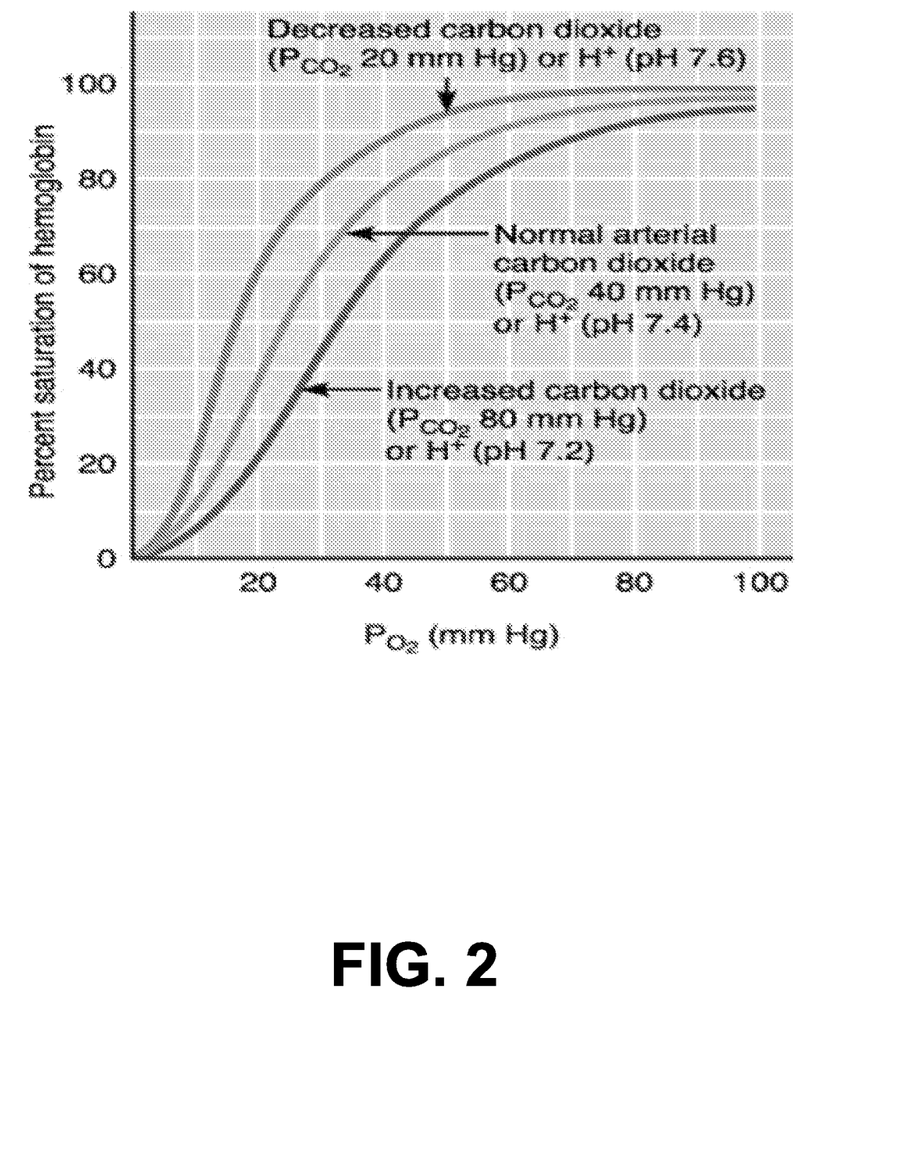
FIG. 2 illustrates a plot of oxygen saturation versus partial pressure of oxygen in arterial blood.

By way of illustration, FIG. 2 shows several plots of oxygen saturation versus partial pressure of oxygen in arterial blood. As can be seen in FIG. 2, the conversion between these two parameters is not linear. As such, intermittent measurements of partial pressure of oxygen in arterial blood can be used to calibrate and/or adjust a conversion of measurements of oxygen saturation to estimations of partial pressure of oxygen in arterial blood. Further, it will be appreciated from FIG. 2 that the relationship between oxygen saturation and partial pressure of oxygen in arterial blood is impacted by partial pressure of carbon dioxide in arterial blood and/or blood pH. Accordingly, measurements of partial pressure of carbon dioxide in arterial blood and/or blood pH can be used to further calibrate and/or adjust a conversion of measurements of oxygen saturation to estimations of partial pressure of oxygen in arterial blood.

Referring back to FIG. 1, oxygen fraction module 40 is configured to determine a therapeutic fraction of inspired oxygen. The therapeutic fraction of inspired oxygen is the fraction of inspired oxygen that will maintain the oxygenation of subject 12 at a therapeutically beneficial level. The control module 32 is configured to implement the therapeutic fraction of inspired oxygen determined by oxygen fraction module 40 by controlling the pressure generator 14 to adjust the concentration of oxygen in the pressurized flow of breathable gas that corresponds to the therapeutic fraction of inspired oxygen.

In one embodiment, determining the therapeutic fraction of inspired oxygen includes determining the fraction of inspired oxygen that will maintain oxygen saturation of subject 12 at a therapeutically beneficial level. In one embodiment, oxygen fraction module 40 determines the therapeutic fraction of inspired oxygen to maintain partial pressure of oxygen in arterial blood at a therapeutically beneficial level. The oxygen fraction module 40 is configured to determine the therapeutic fraction of inspired oxygen in a feedback loop that uses oxygen saturation, partial pressure of oxygen in arterial blood, and/or some other metric indicating oxygenation as the input. If the metric used indicates that oxygenation is too high, the therapeutic fraction of inspired oxygen is adjusted downward from its current level. If the metric used indicates that oxygenation is too low, the fraction of inspired oxygen is adjusted upward from its current level.

The oxygen fraction module 40 is configured such that adjustments to the therapeutic fraction of inspired oxygen are constrained by oxygen fraction constraints. The oxygen fraction constraints may constrain one or more of a rate of change of the therapeutic fraction of inspired oxygen (e.g., over a sliding window in time), an adjustment increment of the therapeutic fraction of inspired oxygen, a maximum level of the therapeutic fraction of inspired oxygen, a minimum level of the therapeutic fraction of inspired oxygen, temporal adjacency of adjustments to the therapeutic fraction of inspired oxygen, and/or may otherwise constrain adjustments to the determination of the therapeutic fraction of inspired oxygen. An oxygen fraction constraint that constrains the rate of change of the therapeutic fraction of inspired oxygen may set a maximum rate of change. An oxygen fraction constraint that constrains an adjustment increment of the therapeutic fraction of inspired oxygen may set a standard increment amount, may set a minimum increment amount, may set a maximum increment amount, and/or may otherwise constrain adjustment increments. An oxygen fraction constraint that constrains a temporal adjacency of adjustments to the therapeutic fraction of inspired oxygen may set a minimum waiting period from a previous adjustment until a next adjustment can be made, and/or may otherwise constrain the temporal adjacency of adjustments to the therapeutic fraction of inspired oxygen.

In one embodiment, oxygen fraction module 40 is configured to determine the therapeutic fraction of inspired oxygen solely (or substantially so) to maintain oxygenation in subject 12. In one embodiment, oxygen fraction module 40 is configured to systematically decrease the therapeutic fraction of inspired oxygen over time. The systematic decrease of the therapeutic fraction of inspired oxygen is performed such that subject 12 is gradually weaned from the extra oxygen included in pressurized flow of breathable gas.

The PEEP module 42 is configured to determine a therapeutic positive end expiratory pressure. The therapeutic positive end expiratory pressure is the positive end expiratory pressure that helps maintain oxygenation in the blood of subject 12 at a therapeutically beneficial level. In one embodiment, determining the therapeutic positive end expiratory pressure includes determining the positive end expiratory pressure that helps maintain oxygen saturation of subject 12 at a therapeutically beneficial level. In one embodiment, PEEP module 42 determines the therapeutic positive end expiratory pressure to maintain partial pressure of oxygen in arterial blood at a therapeutically beneficial level. The PEEP module 42 is configured to determine the therapeutic positive end expiratory pressure in a feedback loop that uses oxygen saturation, partial pressure of oxygen in arterial blood, and/or some other metric indicating oxygenation as the input. If the metric used indicates that oxygenation is too high, the therapeutic positive end expiratory pressure is adjusted downward from its current level. If the metric used indicates that oxygenation is too low, the positive end expiratory pressure is adjusted upward from its current level.

The PEEP module 42 is configured such that adjustments to the therapeutic positive end expiratory pressure are constrained by PEEP constraints. The positive end expiratory pressures may constrain one or more of a rate of change of the therapeutic positive end expiratory pressure (e.g., over a sliding window in time), an adjustment increment of the therapeutic positive end expiratory pressure, a maximum level of the therapeutic positive end expiratory pressure, a minimum level of the therapeutic positive end expiratory pressure, temporal adjacency of adjustments to the therapeutic positive end expiratory pressure, and/or may otherwise constrain adjustments to the determination of the therapeutic positive end expiratory pressure. A PEEP constraint that constrains the rate of change of the therapeutic positive end expiratory pressure may set a maximum rate of change. A PEEP constraint that constrains an adjustment increment of the therapeutic positive end expiratory pressure may set a standard increment amount, may set a minimum increment amount, may set a maximum increment amount, and/or may otherwise constrain adjustment increments. A PEEP constraint that constrains a temporal adjacency of adjustments to the therapeutic positive end expiratory pressure may set a minimum waiting period from a previous adjustment until a next adjustment can be made, and/or may otherwise constrain the temporal adjacency of adjustments to the therapeutic positive end expiratory pressure.

In one embodiment, PEEP module 42 is configured to determine the therapeutic positive end expiratory pressure solely (or substantially so) to maintain oxygenation in subject 12. In one embodiment, PEEP module 42 is configured to systematically decrease the therapeutic positive end expiratory pressure over time. The systematic decrease of the therapeutic positive end expiratory pressure is performed such that subject 12 is gradually weaned from the pressurized delivery of gas embodied by the pressurized flow of breathable gas.

The exhalation module 44 is configured to determine an expiratory pressure level that corresponds to the therapeutic positive end expiratory pressure. This may be determined in a feedback manner by using the positive end expiratory pressure determined by breathing parameter module 34 as an input. As adjustments are made to the therapeutic positive end expiratory pressure, corresponding adjustments may be made to the expiratory pressure level determined by exhalation module 44. The control module 32 implements the expiratory pressure level determined by exhalation module 44 to provide the pressurized flow of breathable gas to the subject at the expiratory pressure level during expiration. This may maintain the positive end expiratory pressure of subject 12 at the therapeutic positive end expiratory pressure.

The interface module 46 is configured to receive selection and/or entry of control inputs from a user via user interface 18. The control inputs may dictate one or more aspects of the operation system 10. By way of non-limiting example, the control inputs may define one or more of oxygen fraction constraints, PEEP constraints, an oxygenation metric to be used to determine the therapeutic fraction of inspired oxygen and/or the therapeutic positive end expiratory pressure, activation and deactivation for the mode of operation for positive end expiratory pressure control, an activation or a deactivation of a wean mode of operation, alarm settings and limits for oxygen low oxygen saturation and high or maximum fraction of inspired oxygen and high or maximum PEEP level, and/or other factors in the operation of system 10.

Figure 3:
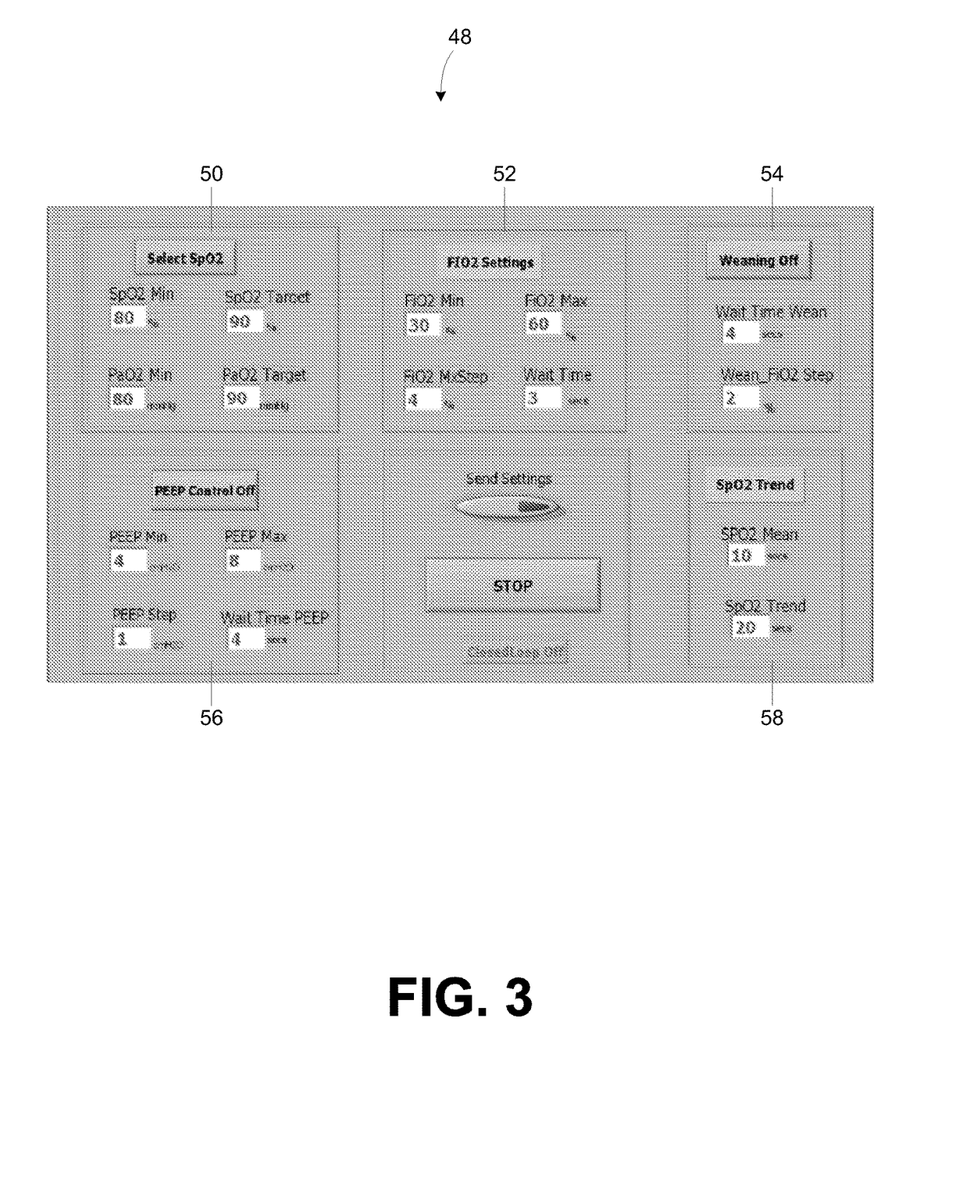
FIG. 3 illustrates a user interface configured to receive control inputs to a system configured to deliver a pressurized flow of breathable gas to the lungs of a subject.

By way of illustration, FIG. 3 illustrates a graphical user interface 48 which may be generated to receive selection and/or entry of control inputs from a user. The graphical user interface 48 may be presented to the user via a user interface that is the same as or similar to user interface 18 (shown in FIG. 1 and described above). The graphical user interface 48 may include an oxygenation metric field 50, an oxygen fraction constraint field 52, a wean mode field 54, a PEEP constraint field 56, an oxygenation determination field 58, and/or other fields.

The oxygenation metric field 50 is configured to receive selection and/or entry of control inputs related to the oxygenation metric implemented in a feedback manner to determine adjustments to a therapeutic fraction of inspired oxygen. The control inputs may include a metric selection, a minimum oxygenation level, a therapeutic oxygenation level, and/or other control inputs. A metric selection designates an oxygenation metric to be implemented to determine adjustments to the therapeutic fraction of inspired oxygen.

The oxygenation metric field 50 may be configured to receive selection and/or entry of oxygen saturation, partial pressure of oxygen in arterial blood, and/or other metrics to be implemented. A minimum oxygenation level may set a minimum level for the selected oxygenation metric. A therapeutic oxygenation level may set the level of the selected oxygenation metric that the therapeutic fraction of inspired oxygen is adjusted to maintain.

The oxygen fraction constraint field 52 is configured to receive selection and/or entry of control inputs related to the therapeutic fraction of inspired oxygen, oxygen fraction constraints, and/or other control inputs. The oxygen fraction constraints received through oxygen fraction constraint field 52 may include one or more of a rate of change constraint, an adjustment increment constraint, a maximum level constraint, a minimum level constraint, a wait time constraint, and/or other oxygen fraction constraints.

The wean mode field 54 is configured to receive selection and/or entry of a wean mode activation/deactivation, a wean wait time, a wean adjustment constraint, and/or other control inputs. A wean wait time may dictate how long is taken between decreases in the therapeutic fraction of inspired oxygen and/or the therapeutic positive end expiratory pressure. A wean adjustment constraint may define the adjustment increment used to decrease the therapeutic fraction of inspired oxygen and/or the therapeutic positive end expiratory pressure during weaning.

The PEEP constraint field 56 is configured to receive an activation/deactivation of PEEP mode, selection and/or entry of control inputs related to the therapeutic positive end expiratory pressure, PEEP constraints, and/or other control inputs. An activation/deactivation of PEEP mode selectively activates and/or deactivates the dynamic determination of the therapeutic positive end expiratory pressure based on oxygenation. If the PEEP mode is deactivated, then the therapeutic positive end expiratory pressure may be set to a fixed level, and/or determined based on other inputs. The PEEP constraints received through PEEP constraint field 56 may include one or more of a rate of change constraint, an adjustment increment constraint, a maximum level constraint, a minimum level constraint, a wait time constraint, and/or other PEEP constraints.

The oxygenation determination field 58 is configured to receive control inputs dictating the timing at which the oxygenation metric is determined. These control inputs may include a mean value sampling period, an oxygenation trend sampling period, and/or other control inputs.

Figure 4:
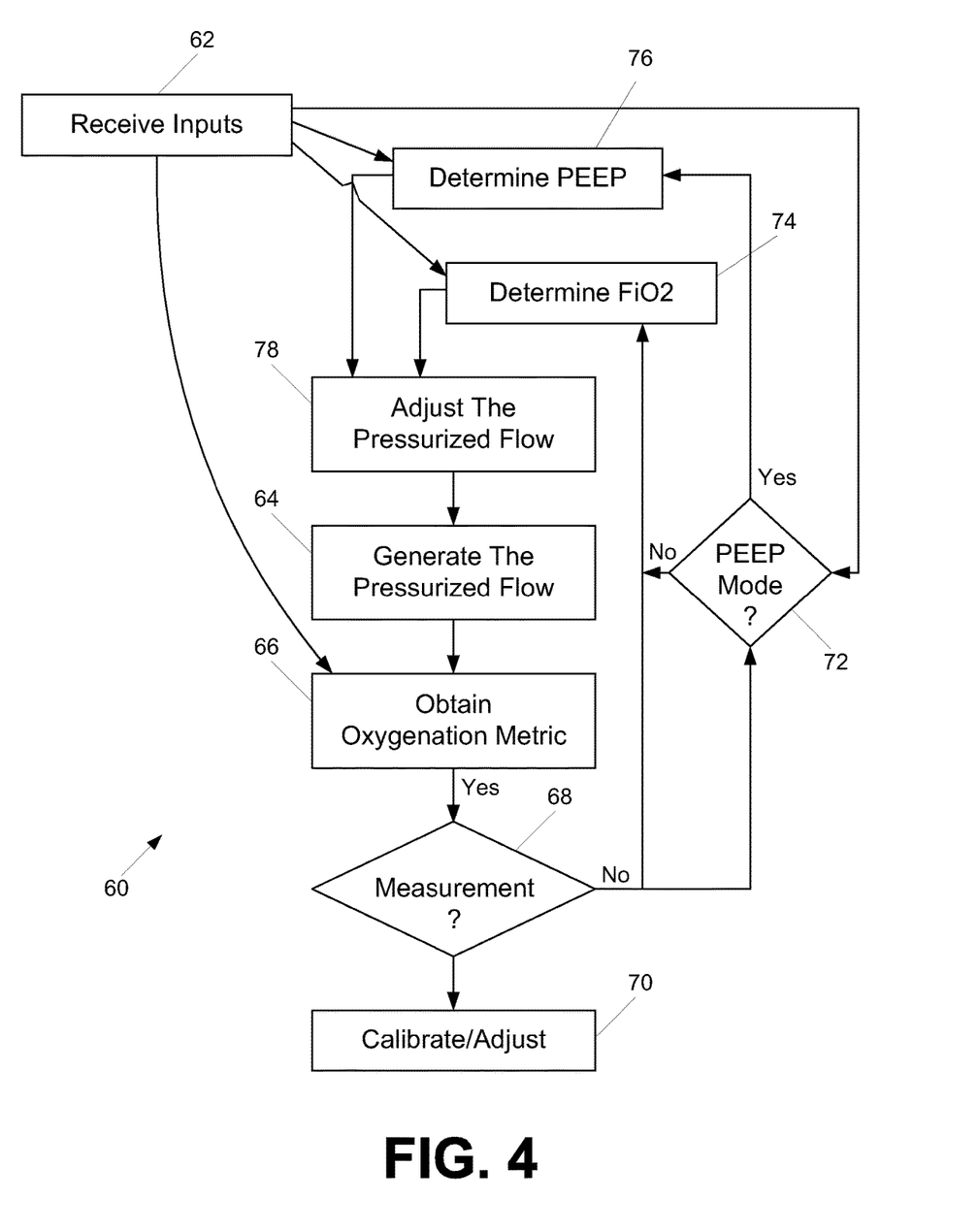
FIG. 4 illustrates a method of maintaining oxygenation of a subject.

FIG. 4 illustrates a method 60 of maintaining oxygenation of a subject. The operations of method 60 presented below are intended to be illustrative. In some embodiments, method 60 may be accomplished with one or more additional operations not described, and/or without one or more of the operations discussed. Additionally, the order in which the operations of method 60 are illustrated in FIG. 4 and described below is not intended to be limiting.

In some embodiments, some or all of the operations of method 60 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 60 in response to instructions stored electronically on an electronic storage medium. The one or more processing devices may include one or more devices configured through hardware, firmware, and/or software to be specifically designed for execution of one or more of the operations of method 60.

At an operation 62, one or more control inputs are received from a user. The control inputs dictate, influence, and/or define one or more aspects of the therapy to be received by the subject. The control inputs may include one or more of a therapeutic oxygenation level, an oxygenation metric selection, a maximum fraction of inspired oxygen level, a minimum fraction of inspired oxygen level, a PEEP constraint, a PEEP mode activation/deactivation, a wean mode activation/deactivation, and/or other control inputs. In one embodiment, operation 62 is performed by an interface module similar to or the same as interface module 46 (shown in FIG. 1 and described above) which receives the one or more control inputs via a user interface similar to or the same as user interface 18 and/or graphical user interface 48 (shown in FIGS. 1 and 3, respectively, and described above).

At an operation 64, a pressurized flow of breathable gas is generated for delivery to the lungs of the subject. One or more parameters of the pressurized flow of breathable gas can be controlled in accordance with a therapy regimen. In one embodiment, operation 64 is performed by a pressure generator similar to or the same as pressure generator 14 (shown in FIG. 1 and described above) under the control of a control module similar to or the same as control module 32 (shown in FIG. 1 and described above).

At an operation 66, an oxygenation metric is obtained that indicates an amount of oxygen present in the blood of the subject. The oxygenation metric may include oxygen saturation, partial pressure of oxygen in arterial blood, and/or other oxygenation metrics. The determination of the oxygenation metric may include an estimation of the oxygenation metric. The oxygenation metric obtained at operation 66 may be dictated by a control input received at operation 62 indicating a specific oxygenation metric. Obtaining the oxygenation metric may include determining the oxygenation metric (e.g., based on sensor output signals), and/or receiving a determination of the oxygenation metric from an external component (e.g., from a patient monitor similar to or the same as patient monitor 31 shown in FIG. 1 and described above). In one embodiment, operation 66 may be performed by a oxygen saturation module and/or an arterial oxygen module similar to or the same as oxygen saturation module 36 and/or arterial oxygen module 38, respectively (shown in FIG. 1 and described above).

At an operation 68, a determination is made as to whether the determination of the oxygenation metric should be calibrated and/or adjusted. Calibration and/or adjustment may occur at the time responsive to entry and/or reception of a measurement of an oxygenation metric that is taken only intermittently. The measurement may be taken intermittently because it is invasive to the subject. Responsive to calibration and/or adjustment being appropriate at operation 68, method 60 proceeds to an operation 70.

At operation 70, the determination of the oxygenation metric is calibrated and/or adjusted. The calibrated/adjusted determination may be the estimation of partial pressure of oxygen in arterial blood determined as a function of oxygen saturation, as described here. In one embodiment, operation 70 is performed by an arterial oxygen module similar to or the same as arterial oxygen module 38 (shown in FIG. 1 and described above).

From operation 68 or from operation 70, method 60 proceeds to an operation 72 and an operation 74. At operation 72, a determination is made as to whether a therapeutic positive end expiratory pressure should be determined based on the oxygenation metric determined at operation 66. This may be determined based on whether PEEP mode is activated or deactivated. Activation or deactivation of PEEP mode may be dictated by control inputs received at operation 62. Responsive to a determination that the therapeutic positive end expiratory pressure should be determined based on the oxygenation metric, method 60 proceeds to an operation 76. Responsive to a determination that the therapeutic positive end expiratory pressure should not be determined based on the oxygenation metric, method 60 proceeds to operation 74.

At operation 74, a therapeutic fraction of inspired oxygen is determined based on the oxygenation metric determined at operation 66. The therapeutic fraction of inspired oxygen is determined to maintain the oxygenation metric at a therapeutic level (e.g., received at operation 62). Responsive to a fraction of inspired oxygen wean mode activation being received at operation 62, the therapeutic fraction of inspired oxygen may be decremented in an attempt to wean the subject from the therapy provided by method 60. If the therapeutic fraction of inspired oxygen needs to be adjusted from its previous level, adjustment is constrained by oxygen fraction constraints received from the user at operation 62. In one embodiment, operation 74 is performed by a oxygen fraction module similar to or the same as oxygen fraction module 40 (shown in FIG. 1 and described above).

At operation 76, the therapeutic positive end expiratory pressure is determined based on the oxygenation metric determined at operation 66. The therapeutic positive end expiratory pressure is determined to maintain the oxygenation metric at a therapeutic level (e.g., received at operation 62). Responsive to a PEEP wean mode activation being received at operation 62, the therapeutic positive end expiratory pressure may be decremented in an attempt to wean the subject from the therapy provided by method 60. In the event that the therapeutic positive end expiratory pressure needs to be adjusted from its previous level, adjustment is constrained by PEEP constraints received from the user at operation 62. In one embodiment, operation 76 is performed by a PEEP module similar to or the same as PEEP module 42 (shown in FIG. 1 and described above).

At an operation 78, the pressurized flow of breathable gas is adjusted based on the therapeutic fraction of inspired oxygen determined at operation 74 and/or the therapeutic positive end expiratory pressure determined at operation 76. In one embodiment, operation 78 is performed by a pressure generator similar to or the same as pressure generator 14 (shown in FIG. 1 and described above) under the control of a control module similar to or the same as control module 32 (shown in FIG. 1 and described above).

Details included herein are for the purpose of illustration based on what is currently considered to be the most practical and preferred embodiments, it is to be understood that such detail is solely for that purpose and that the scope of this specification is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to control a fraction of inspired oxygen in a pressurized flow of breathable gas delivered to lungs of a subject, the system comprising:

a pressure generator configured to generate a pressurized flow of breathable gas for delivery to the lungs of a subject, the pressure generator being configured to selectively control the fraction of inspired oxygen of the subject by adjusting a concentration of oxygen in the pressurized flow of breathable gas;

a user interface;

one or more processors configured to execute computer program modules, the computer program modules comprising:

a blood oxygen module configured to determine a level of an oxygenation metric representing an amount of oxygen present in blood of the subject;

an oxygen fraction module configured to dynamically determine a therapeutic fraction of inspired oxygen for the subject in accordance with a therapy regimen, wherein the oxygen fraction module is configured to dynamically determine the therapeutic fraction of inspired oxygen needed to maintain a therapeutically beneficial level of oxygenation (i) in accordance with the therapy regimen or (ii) to wean the subject from therapy (iii) based on the determined level of the oxygenation metric in a feedback manner;

an interface module configured to receive oxygen fraction constraints from a user via the user interface, wherein the oxygen fraction module is further configured such that the one oxygen fraction constraints received from the user via the user interface constrain the dynamic determination of the therapeutic fraction of inspired oxygen, wherein the oxygen fraction constraints comprise: (i) an amount of time between adjustments to the dynamically determined therapeutic fraction of inspired oxygen, and (ii) a maximum magnitude of a rate of change of the dynamically determined therapeutic fraction of inspired oxygen;

a positive end expiratory pressure ("PEEP") module configured to dynamically determine a therapeutic positive end expiratory pressure pursuant to and within PEEP constraints received from the user via the user interface, wherein the PEEP constraints comprise: (i) an amount of time between adjustments to the dynamically determined therapeutic positive end expiratory pressure, and (ii) a maximum magnitude of a rate of change of the dynamically determined therapeutic positive end expiratory pressure;

an exhalation module configured to determine an expiratory pressure for the pressurized flow of breathable gas that will maintain a positive end expiratory pressure of the subject at the dynamically determined therapeutic positive end expiratory pressure; and a control module configured to control the pressure generator to adjust the concentration of oxygen in the pressurized flow of breathable gas to automatically and dynamically change the fraction of inspired oxygen of the subject in accordance with the dynamically determined therapeutic fraction of inspired oxygen, wherein the changes to the fraction of inspired oxygen are within the received oxygen fraction constraints, and further configured to provide the pressurized flow of breathable gas with the expiratory pressure determined by the exhalation module during expiration such that the dynamically determined therapeutic positive end expiratory pressure is maintained.

2. The system of claim 1, wherein the interface module is configured such that the oxygen fraction constraints comprise a maximum magnitude for an incremental change to the dynamically determined therapeutic fraction of inspired oxygen.

3. The system of claim 1, wherein the blood oxygen module is configured such that the oxygenation metric comprises (i) oxygen saturation or (ii) partial pressure of oxygen in arterial blood.

4. The system of claim 1, wherein the PEEP module is further configured to dynamically determine the therapeutic positive end expiratory pressure in accordance with the therapy regimen based on the determined level of the oxygenation metric in a feedback manner.

5. A method of controlling a fraction of inspired oxygen in a pressurized flow of breathable gas delivered to the lungs of a subject, the method comprising:
 generating a pressurized flow of breathable gas for delivery to the lungs of a subject;
 obtaining a level of an oxygenation metric indicating an amount of oxygen present in blood of the subject;
 receiving one or more oxygen fraction constraints from a user via a user interface, wherein the one or more oxygen fraction constraints comprise: one or more of (i) an amount of time between adjustments to the dynamically determined therapeutic fraction of inspired oxygen, and (ii) a maximum magnitude of rate of change of the dynamically determined therapeutic fraction of inspired oxygen;
 dynamically determining a therapeutic fraction of inspired oxygen for the subject in accordance with a therapy regimen needed to maintain a therapeutically beneficial level of oxygenation (i) in accordance with the therapy regimen or (ii) to wean the subject from therapy (iii) based on the obtained level of the oxygenation metric in a feedback manner, wherein the oxygen fraction constraints received from the user constrain the dynamic determination of the therapeutic fraction of inspired oxygen; and
 dynamically determining a therapeutic positive end expiratory pressure for the subject in accordance with a therapy regimen, wherein the therapy regimen comprises one or more positive end expiratory pressure constraints received from the user via the user interface, wherein the positive end expiratory pressure constraints comprise: (i) an amount of time between adjustments to the dynamically determined therapeutic positive end expiratory pressure, and (ii) a maximum magnitude of a rate of change of the dynamically determined therapeutic positive end expiratory pressure;
 dynamically determining an expiratory pressure for the pressurized flow of breathable gas that will maintain a positive end expiratory pressure of the subject at the dynamically determined therapeutic positive end expiratory pressure;
 adjusting a concentration of oxygen in the pressurized flow of breathable gas to automatically and dynamically change the fraction of inspired oxygen of the subject in accordance with the dynamically determined therapeutic fraction of inspired oxygen, wherein the changes to the fraction of inspired oxygen are within the constrained by-received oxygen fraction constraints; and
 providing the pressurized flow of breathable gas during expiration with the expiratory pressure dynamically determined to maintain the dynamically determined therapeutic positive end expiratory pressure.

6. The method of claim 5, wherein the oxygen fraction constraints comprise a maximum magnitude for an incremental change to the dynamically determined therapeutic fraction of inspired oxygen.

7. The method of claim 5, wherein the oxygenation metric comprises (i) oxygen saturation or (ii) partial pressure of oxygen in arterial blood.

8. The method of claim 5, wherein dynamically determining the therapeutic positive end expiratory pressure further comprises dynamically determining the therapeutic positive end expiratory pressure in accordance with the therapy regimen based on the obtained level of the oxygenation metric in a feedback manner.

9. A system for controlling the fraction of inspired oxygen in a pressurized flow of breathable gas delivered to lungs of a subject, the system comprising:
 means for generating a pressurized flow of breathable gas for delivery to the lungs of a subject;
 means for obtaining a level of an oxygenation metric indicating an amount of oxygen present in the blood of the subject;
 means for receiving one or more oxygen fraction constraints from a user via a user interface, wherein the oxygen fraction constraints comprise one or more of (i) an amount of time between adjustments to the dynamically determined therapeutic fraction of inspired oxygen, and (ii) a maximum magnitude of a rate of change of the dynamically determined therapeutic fraction of inspired oxygen;
 means for dynamically determining a therapeutic fraction of inspired oxygen for the subject in accordance with a therapy regimen needed to maintain a therapeutically beneficial level of oxygenation (i) in accordance with the therapy regimen or (ii) to wean the subject from therapy (iii) based on the obtained level of the oxygenation metric indicating the amount of oxygen present in the blood of the subject in a feedback manner, wherein the oxygen fraction constraints received from the user constrain the dynamic determination of the therapeutic fraction of inspired oxygen;
 means for dynamically determining a therapeutic positive end expiratory pressure pursuant to and within positive end expiratory pressure constraints received from the user via the user interface, wherein the positive end expiratory pressure constraints comprise: (i) an amount of time between adjustments to the dynamically determined therapeutic positive end expiratory pressure, and (ii) a maximum magnitude of a rate of change of the dynamically determined therapeutic positive end expiratory pressure;
 means for dynamically determining an expiratory pressure for the pressurized flow of breathable gas that will maintain a positive end expiratory pressure of the subject at the dynamically determined therapeutic positive end expiratory pressure;
 means for adjusting a concentration of oxygen in the pressurized flow of breathable gas to automatically and dynamically change the fraction of inspired oxygen of the subject in accordance with the dynamically determined therapeutic fraction of inspired oxygen wherein the changes to the fraction of inspired oxygen are within the constrained by received oxygen fraction constraints; and
 means for providing the pressurized flow of breathable gas during expiration with the expiratory pressure dynamically determined to maintain the dynamically determined therapeutic positive end expiratory pressure.

10. The system of claim 9, wherein the oxygen fraction constraints comprise a maximum magnitude for an incremental change to the dynamically determined therapeutic fraction of inspired oxygen.

11. The system of claim 9, wherein the oxygenation metric comprises (i) oxygen saturation and/or (ii) partial pressure of oxygen in arterial blood.

12. The system of claim 9, wherein means for dynamically determining the therapeutic positive end expiratory pressure is further configured to dynamically determine the therapeutic positive end expiratory pressure in accordance with the therapy regimen based on obtained level of the oxygenation metric indicating the amount of oxygen present in the blood of the subject in a feedback manner.

* * * * *